United States Patent [19]

Fischer et al.

[11] Patent Number: 5,350,861
[45] Date of Patent: Sep. 27, 1994

[54] SUBSTITUTED 3-ARYL-PYRROLIDINE-2,4-DIONES

[75] Inventors: Reiner Fischer, Monheim; Hermann Uhr, Leverkusen; Arno Widdig, Odenthal-Blecher; Stefan Dutzmann, Hilden; Christoph Erdelen, Leichlingen; Ulrike Wachendorff-Neumann, Monheim; Klaus Schaller, Wuppertal, all of Fed. Rep. of Germany

[73] Assignee: Bayer Aktiengesellschaft, Leverkusen, Fed. Rep. of Germany

[21] Appl. No.: 821,801

[22] Filed: Jan. 16, 1992

[30] Foreign Application Priority Data

Jan. 26, 1991 [DE] Fed. Rep. of Germany ....... 4102339

[51] Int. Cl.$^5$ ................. C07D 207/38; C07D 207/40; A01N 43/36
[52] U.S. Cl. .................................................. 548/544
[58] Field of Search .................. 514/424, 425; 548/544

[56] References Cited

U.S. PATENT DOCUMENTS

| | | | |
|---|---|---|---|
| 4,551,547 | 11/1985 | Wheller | 560/255 |
| 5,045,560 | 9/1991 | Fischer et al. | 514/425 |
| 5,102,904 | 4/1992 | Kameswaran | 514/424 |

FOREIGN PATENT DOCUMENTS

| | | |
|---|---|---|
| 0377893 | 7/1990 | European Pat. Off. . |
| 0442077 | 8/1991 | European Pat. Off. . |
| 0456063 | 11/1991 | European Pat. Off. . |

*Primary Examiner*—David B. Springer
*Attorney, Agent, or Firm*—Sprung Horn Kramer & Woods

[57] ABSTRACT

There are provided new substituted 3-aryl-pyrrolidine-2,4-diones of the formula

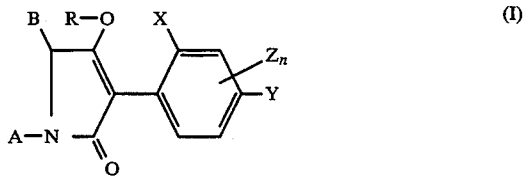

(I)

in which
X represents hydrogen, alkyl, halogen or alkoxy,
Y represents hydrogen, alkyl, halogen, alkoxy or halogenoalkyl,
Z represents alkyl, halogen or alkoxy,
n represents a number from 0–3,
R represents hydrogen or the groups $$-CO-R^1, -CO-O-R^2$$

in which
$R^1$ and $R^2$ have the meanings given in the text of the application,
A represents optionally halogen-substituted alkyl, alkenyl, alkinyl, alkoxyalkyl, polyalkoxyalkyl, alkylthioalkyl and cycloalkyl which is optionally interrupted by hetero atoms, or represents arylakyl which is optionally substituted by halogen, alkyl, halogenoalkyl, alkoxy or nitro,
B represents optionally substituted aryl or benzyl.

The new compounds of the formula (I) have highly pronounced insecticidal, acaricidal, fungicidal and antimycotic properties.

6 Claims, No Drawings

SUBSTITUTED 3-ARYL-PYRROLIDINE-2,4-DIONES

The invention relates to new substituted 3-aryl-pyrrolidine-2,4-diones, to a plurality of processes for their preparation and to their use as insecticides, acaricides, fungicides and antimycotics.

Pharmaceutical properties of 3-acyl-pyrrolidine-2,4-diones have previously been described (S. Suzuki et. al. Chem. Pharm. Bull. 15 1120 (1967)). Furthermore N-phenylpyrrolidine-2,4-diones were synthesised by R. Schmierer and H. Mildenberger Liebigs Ann. Chem. 1985 1095. A biological activity of these compounds has not been described.

EP-A 0,262,399 discloses compounds of a similar structure 3-aryl-pyrrolidine-2,4-diones), but no insecticidal or acaricidal action has become known.

New substituted 3-aryl-pyrrolidine-2,4-diones have now been found, which are described by formula (I)

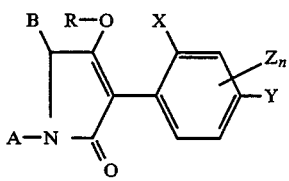

in which

X represents hydrogen, alkyl, halogen or alkoxy,
Y represents hydrogen, alkyl, halogen, alkoxy or halogenoalkyl,
Z represents alkyl, halogen or alkoxy,
n represents a number from 0–3,
R represents hydrogen or the groups

in which $R^1$ represents optionally halogen-substituted alkyl, alkenyl, alkoxyalkyl, alkylthioalkyl, polyalkoxyalkyl and cycloalkyl which can be interrupted by hetero atoms, or represents optionally substituted phenyl, optionally substituted phenylalkyl, substituted hetaryl, substituted phenoxyalkyl and substituted hetaryloxyalkyl and $R^2$ represents optionally halogen-substituted alkyl, alkenyl, alkoxyalkyl or polyalkoxyalkyl and optionally substituted phenyl, A represents optionally halogen-substituted alkyl, alkenyl, alkinyl, alkoxyalkyl, polyalkoxyalkyl, alkylthioalkyl or cycloalkyl which is optionally interrupted by hetero atoms, or represents arylalkyl which is optionally substituted by halogen, alkyl, halogenoalkyl, alkoxy or nitro, B represents optionally substituted aryl or optionally substituted benzyl and the pure enantiomeric forms of compounds of the formula (I).

The following sub-groups may be defined in what follows:

(Ia): Compounds of the formula (I) in which R=hydrogen,
(Ib): Compounds of the formula (I) in which R=COR$^1$,
(Ic): Compounds of the formula (I) in which R=COOR$^2$.

Furthermore, it has been found that the new substituted 3-aryl-pyrrolidine-2,4-diones, or enols thereof of the formula (Ia)

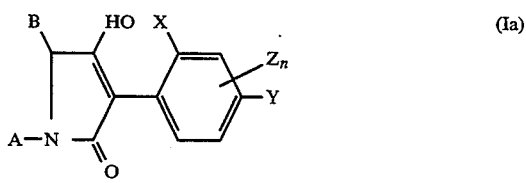

in which A, B, X, Y, Z and n have the abovementioned meaning, are obtained when (A)
N-acylamino acid esters of the formula (II)

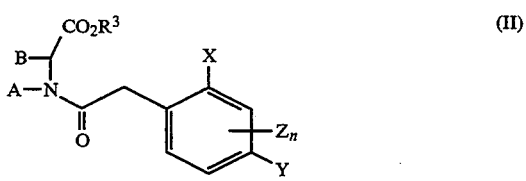

in which
A, B, X, Y, Z and n have the abovementioned meaning and
$R^3$ represents alkyl
are subjected to an intramolecular condensation reaction in the presence of a diluent and in the presence of a base.

(B)
Moreover, it has been found that compounds of the formula (Ib)

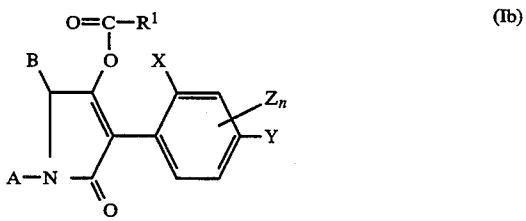

in which A, B, X, Y, Z, $R^1$ and n have the abovementioned meaning are obtained when compounds of the formula (Ia)

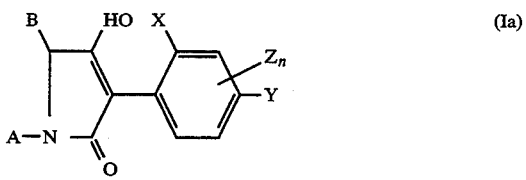

in which
A, B, X, Y, Z and n have the abovementioned meaning are reacted
a) with acid halides of the general formula (III)

in which
$R^1$ has the abovementioned meaning and

Hal represents halogen, in particular chlorine and bromine, if appropriate in the presence of a diluent and if appropriate in the presence of an acid-binding agent, or β) with carboxylic anhydrides of the general formula (IV)

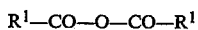

$$R^1-CO-O-CO-R^1 \quad (IV)$$

in which $R^1$ has the abovementioned meaning, if appropriate in the presence of a diluent and if appropriate in the presence of an acid-binding agent.

(C)

Furthermore, it has been found that compounds of the formula (Ic)

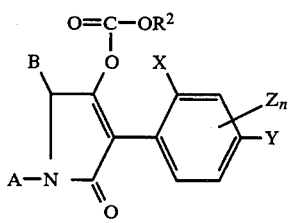

in which

A, B, X, Y, Z, $R^2$ and n have the abovementioned meaning are obtained when compounds of the formula (Ia)

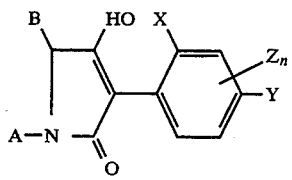

in which

A, B, X, Y, Z and n have the abovementioned meaning, are reacted with chloroformic esters of the general formula (V)

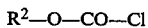

$$R^2-O-CO-Cl \quad (V)$$

in which $R^2$ has the abovementioned meaning, if appropriate in the presence of a diluent and if appropriate in the presence of an acid-binding agent.

Surprisingly, it has been found that the new substituted 3-arylpyrrolidine-2,4-diones of the formula (I) are distinguished by very good insecticidal, acaricidal, fungicidal and antimycotic actions.

Preferred substituted 3-aryl-pyrrolidine-2,4-diones of the formula (I) are those in which X represents hydrogen, $C_1-C_6$-alkyl, halogen or $C_1-C_6$-alkoxy, Y represents hydrogen, $C_1-C_6$-alkyl, halogen, $C_1-C_6$-alkoxy oxy or $C_1-C_3$-halogenoalkyl, Z represents $C_1-C_6$-alkyl, halogen or $C_1-C_6$-alkoxy, n represents a number from 0-3, R represents hydrogen (Ia) or the groups of the formula

$$-CO-R^1 \quad (Ib)$$

or $$-CO-O-R^2 \quad (Ic)$$

in which $R^1$ represents optionally halogen-substituted $C_1-C_{20}$-alkyl, $C_2-C_{20}$-alkenyl, $C_1-C_8$-alkoxy-$C_2-C_8$-alkyl, $C_1-C_8$-alkylthio-$C_2-C_8$-alkyl, $C_1-C_8$-polyalkoxy-$C_2-C_8$-alkyl and cycloalkyl which has 3-8 ring atoms and which can be interrupted by oxygen and/or sulphur, or represents phenyl which is optionally substituted by halogen, nitro, $C_1-C_6$-alkyl, $C_1-C_6$-alkoxy, $C_1-C_6$-halogenoalkyl or $C_1-C_6$-halogenoalkoxy;

or represents phenyl-$C_1-C_6$-alkyl which is optionally substituted by halogen, $C_1-C_6$-alkyl, $C_1-C_6$-alkoxy, $C_1-C_6$-halogenoalkyl or $C_1-C_6$-halogenoalkoxy, or represents hetaryl which is optionally substituted by halogen and $C_1-C_6$-alkyl, or represents phenoxy-$C_1-C_6$-alkyl which is optionally substituted by halogen and $C_1-C_6$-alkyl, or represents hetaryloxy-$C_1-C_6$-alkyl which is optionally substituted by halogen, amino and $C_1-C_6$-alkyl, $R^2$ represents optionally halogen-substituted $C_1-C_{20}$-alkyl, $C_2-C_{20}$-alkenyl, $C_1-C_8$alkoxy-$C_2-C_8$-alkyl or $C_1-C_8$-polyalkoxy-$C_2-C_8$-alkyl, or represents phenyl which is optionally substituted by halogen, nitro, $C_1-C_6$-alkyl, $C_1-C_6$-alkoxy or $C_1-C_6$-halogenoalkyl, A represents optionally halogen-substituted straight-chain or branched $C_1-C_{12}$-alkyl, $C_3-C_8$-alkenyl, $C_3-C_8$-alkinyl, $C_1-C_{10}$-alkoxy-$C_2-C_8$-alkyl, $C_1-C_8$-polyalkoxy-$C_2-C_8$-alkyl, $C_1-C_{10}$-alkylthio-$C_2-C_8$-alkyl, cycloalkyl which has 3-8 ring atoms and which can be interrupted by oxygen and/or sulphur, or represents aryl-$C_1-C_6$-alkyl which is optionally substituted by halogen, $C_1-C_6$-alkyl, $C_1-C_6$-haloalkyl, $C_1-C_6$-alkoxy or nitro, B represents phenyl or benzyl which are optionally monosubstituted or trisubstituted by identical or different substituents from the series comprising nitro, halogen or in each case for optionally halogen-substituted alkyl or alkoxy, and the pure enantiomeric forms of compounds of the formula (I).

Particularly preferred compounds of the formula (I) are those in which

X represents hydrogen, $C_1-C_4$-alkyl, halogen or $C_1-C_4$-alkoxy,

Y represents hydrogen, $C_1-C_6$-alkyl, halogen, $C_1-C_4$-alkoxy or $C_1-C_2$-halogenoalkyl, Z represents $C_1-C_4$-alkyl, halogen or $C_1-C_4$-alkoxy, n represents a number from 0-3, R represents hydrogen (Ia) or the groups of the formula

$$-CO-R^1 \quad (Ib)$$

or

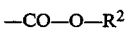

$$-CO-O-R^2 \quad (Ic)$$

in which $R^1$ represents optionally halogen-substituted $C_1-C_{16}$-alkyl, $C_2-C_{16}$-alkenyl, $C_1-C_6$-alkoxy-$C_2-C_6$-alkyl, $C_1-C_6$-alkylthio-$C_2-C_6$-alkyl, $C_1-C_6$-polyalkoxy-$C_2-C_6$-alkyl and cycloalkyl which has 3-7 ring atoms and which can be interrupted by 1-2 oxygen and/or sulphur atoms, or represents phenyl which is optionally substituted by halogen, nitro, $C_1$–$C_4$-alkyl, $C_1$–$C_4$-alkoxy, $C_1$–$C_3$-halogenoalkyl or $C_1$–$C_3$-halogenoalkoxy, or represents phenyl-$C_1$–$C_4$-alkyl which is optionally substituted by halogen, $C_1$–$C_4$-alkyl, $C_1$–$C_4$-alkoxy, $C_1$–$C_3$-halogenoalkyl or $C_1$–$C_3$-halogenoalkoxy, or represents hetaryl which is optionally substituted by halogen and $C_1$–$C_6$-alkyl, or represents phenoxy-$C_1$–$C_5$-alkyl which is optionally substituted by halogen and $C_1$–$C_4$-alkyl, or represents hetaryloxy-$C_1$–$C_5$-alkyl which is optionally substituted by halogen, amino and $C_1$–$C_4$-alkyl, $R^2$ represents optionally halogen-substituted $C_1$–$C_{16}$-alkyl, $C_2$–$C_{16}$-alkenyl, $C_1$–$C_{16}$-alkoxy-$C_2$–$C_6$-alkyl or $C_1$–$C_6$-polyalkoxy-$C_2$–$C_6$-alkyl, or represents phenyl which is optionally substituted by halogen, nitro, $C_1$–$C_4$-alkyl, $C_1$–$C_3$-alkoxy or $C_1$–$C_3$-halogenoalkyl, A represents optionally halogen-substituted straight-chain or branched $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, $C_1$–$C_6$-polyalkoxy-$C_2$–$C_6$-alkyl, $C_1$–$C_8$-alkylthio-$C_2$–$C_6$-alkyl, cycloalkyl which has 3–7 ring atoms and which can be interrupted by 1–2 oxygen and/or sulphur atoms, or represents aryl-$C_1$–$C_4$-alkyl which is optionally substituted by halogen, $C_1$–$C_4$-alkyl, $C_1$–$C_4$-haloalkyl, $C_1$–$C_4$-alkoxy or nitro, B represents phenyl or benzyl which are optionally monosubstituted or disubstituted by identical or different substituents from the series comprising nitro, fluorine, chlorine, bromine, optionally fluorine- or chlorine-substituted $C_1$–$C_4$-alkyl or $C_1$–$C_4$-alkoxy, and the pure enantiomeric forms of compounds of the formula (I).

Very particularly preferred compounds of the formula (I) are those in which

X represents hydrogen, methyl, ethyl, propyl, i-propyl, fluorine, chlorine, bromine, methoxy and ethoxy, Y represents hydrogen, methyl, ethyl, propyl, i-propyl, butyl, i-butyl, tert.-butyl, fluorine, chlorine, bromine, methoxy, ethoxy and trifluoromethyl, Z represents methyl, ethyl, i-propyl, butyl, i-butyl, tert.-butyl, fluorine, chlorine, bromine, methoxy and ethoxy, n represents a number from 0–3, R represents hydrogen (Ia) or the groups of the formula —CO—$R^1$ (Ib)

or

—CO—O—$R^2$ (Ic)

in which $R^1$ represents optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl, $C_1$–$C_4$-alkylthio-$C_2$–$C_6$-alkyl, $C_1$–$C_4$-polyalkoxy-$C_2$–$C_4$-alkyl and cycloalkyl which has 3–6 ring atoms and which can be interrupted by 1–2 oxygen and/or sulphur atoms, or represents phenyl which is optionally substituted by fluorine, chlorine, bromine, methyl, ethyl, propyl, i-propyl, methoxy, ethoxy, trifluoromethyl, trifluoromethoxy or nitro, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy, or represents pyridyl, pyrimidyl, thiazolyl and pyrazolyl which are optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl and thiazolyloxy-$C_1$–$C_4$-alkyl which are optionally substituted by fluorine, chlorine, amino, methyl or ethyl, $R^2$ represents optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl or $C_1$–$C_4$-polyalkoxy-$C_2$–$C_6$-alkyl, or represents phenyl which is optionally substituted by fluorine, chlorine, nitro, methyl, ethyl, propyl, i-propyl, methoxy, ethoxy or trifluoromethyl, A represents optionally halogen-substituted straight-chain or branched $C_1$–$C_8$-alkyl, $C_3$–$C_4$-alkenyl, $C_3$–$C_4$-alkinyl, $C_1$–$C_6$-alkoxy-$C_2$–$C_4$-alkyl, $C_1$–$C_4$-polyalkoxy-$C_2$–$C_4$-alkyl, $C_1$–$C_6$-alkylthio-$C_2$–$C_4$-alkyl or cycloalkyl which has 3–6 ring atoms and which can be interrupted by 1–2 oxygen and/or sulphur atoms, or represents aryl-$C_1$–$C_3$-alkyl which is optionally substituted by fluorine, chlorine, bromine, methyl, ethyl, propyl, iso-propyl, methoxy, ethoxy, trifluoromethyl or nitro, B represents unsubstituted phenyl or benzyl, or represents phenyl or benzyl which are substituted by nitro, fluorine, chlorine or optionally fluorine- or chlorine-substituted $C_1$–$C_2$-alkyl or $C_1$–$C_2$-alkoxy, and the pure enantiomeric forms of compounds of the formula I.

The following substituted 3-aryl-pyrrolidine-2,4-diones of the general formula (I) may be mentioned individually in addition to the compounds mentioned in the Preparation Examples:

TABLE 1

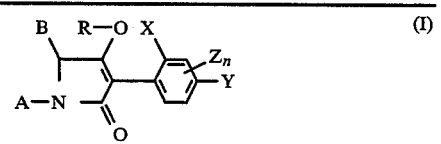

(I)

| A | B | R | X | Y | Zn |
|---|---|---|---|---|---|
| CH3 | Cl-phenyl | H | Cl | Cl | H |
| CH3 | Cl-phenyl | H | Cl | H | 6-Cl |
| CH3 | Cl-phenyl | H | Cl | Cl | H |
| CH3 | Cl-phenyl | H | Cl | H | 6-Cl |
| CH3 | phenyl | H | Cl | Cl | H |
| CH3 | phenyl | H | Cl | H | 6-Cl |

TABLE 1-continued $$\underset{\underset{O}{\overset{A-N}{\|}}}{\overset{B}{\underset{}{\bigg|}}}\overset{R-O}{\underset{}{\bigg|}}\overset{X}{\underset{Y}{\bigg\langle}}\overset{Z_n}{\underset{Y}{\bigg\rangle}} \quad (I)$$

| A | B | R | X | Y | Zn |
|---|---|---|---|---|---|
| CH₃ | 2-Cl-C₆H₄- | H | Cl | Cl | H |
| CH₃ | 2-Cl-C₆H₄- | H | Cl | H | 6-Cl |
| CH₃ | 4-CH₃-C₆H₄- | H | Cl | Cl | H |
| CH₃ | 4-CH₃-C₆H₄- | H | Cl | H | 6-Cl |
| CH₃ | 4-CH₃-C₆H₄-CH₂- | CH₃-C(=O)- | Cl | Cl | H |
| CH₃ | 4-CH₃-C₆H₄-CH₂- | CH₃-C(=O)- | Cl | H | 6-Cl |
| CH₃ | 4-CH₃-C₆H₄-CH₂- | CH₃-C(=O)- | CH₃ | CH₃ | 6-CH₃ |
| CH₃ | 3-CF₃-C₆H₄-CH₂- | CH₃-C(=O)- | Cl | Cl | H |
| CH₃ | 3-CF₃-C₆H₄-CH₂- | CH₃-C(=O)- | Cl | H | 6-Cl |
| CH₃ | 3-CF₃-C₆H₄-CH₂- | CH₃-C(=O)- | CH₃ | CH₃ | 6-CH₃ |
| CH₃ | 3-Cl-C₆H₄-CH₂- | CH₃-C(=O)- | Cl | Cl | H |
| CH₃ | 3-Cl-C₆H₄-CH₂- | CH₃-C(=O)- | Cl | H | 6-Cl |
| CH₃ | 4-Cl-C₆H₄-CH₂- | CH₃-C(=O)- | Cl | Cl | H |
| CH₃ | 4-Cl-C₆H₄-CH₂- | CH₃-C(=O)- | Cl | H | 6-Cl |
| CH₃ | C₆H₅-CH₂- | CH₃-C(=O)- | Cl | Cl | H |
| CH₃ | C₆H₅-CH₂- | CH₃-C(=O)- | Cl | H | 6-Cl |
| CH₃ | C₆H₅-CH₂- | CH₃-C(=O)- | CH₃ | CH₃ | 6-CH₃ |
| CH₃ | 2-Cl-C₆H₄-CH₂- | CH₃-C(=O)- | Cl | Cl | H |
| CH₃ | 2-Cl-C₆H₄-CH₂- | CH₃-C(=O)- | Cl | H | 6-Cl |
| CH₃ | 4-CH₃-C₆H₄- | CH₃-C(=O)- | Cl | Cl | H |
| CH₃ | 4-CH₃-C₆H₄- | CH₃-C(=O)- | Cl | H | 6-Cl |
| CH₃ | 4-CH₃-C₆H₄- | CH₃-C(=O)- | CH₃ | CH₃ | 6-CH₃ |
| CH₃ | 4-CH₃O-C₆H₄- | CH₃-C(=O)- | Cl | Cl | H |
| CH₃ | 4-CH₃O-C₆H₄- | CH₃-C(=O)- | Cl | H | 6-Cl |
| CH₃ | 4-CH₃O-C₆H₄- | CH₃-C(=O)- | CH₃ | CH₃ | 6-CH₃ |
| CH₃ | C₆H₅- | CH₃-C(=O)- | Cl | Cl | H |
| CH₃ | C₆H₅- | CH₃-C(=O)- | Cl | H | 6-Cl |
| CH₃ | 2-Cl-C₆H₄- | CH₃-C(=O)- | Cl | Cl | H |
| CH₃ | 2-Cl-C₆H₄- | CH₃-C(=O)- | Cl | H | 6-Cl |
| CH₃ | 3-Cl-C₆H₄- | CH₃-C(=O)- | Cl | Cl | H |
| CH₃ | 3-Cl-C₆H₄- | CH₃-C(=O)- | Cl | H | 6-Cl |

TABLE 1-continued

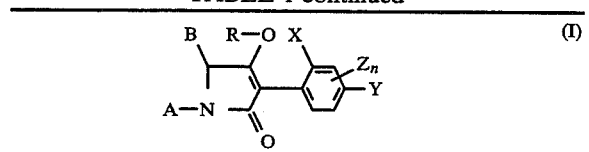

| A | B | R | X | Y | Zn |
|---|---|---|---|---|---|
| CH3 | 4-Cl-C6H4- | CH3-C(=O)- | Cl | Cl | H |
| CH3 | 4-Cl-C6H4- | CH3-C(=O)- | Cl | H | 6-Cl |
| CH3 | 4-CH3O-C6H4- | H | Cl | Cl | H |
| CH3 | 4-CH3O-C6H4- | H | Cl | H | 6-Cl |
| CH3 | 3-Cl-C6H4-CH2- | H | Cl | Cl | H |
| CH3 | 3-Cl-C6H4-CH2- | H | Cl | H | 6-Cl |
| CH3 | 4-Cl-C6H4-CH2- | H | Cl | Cl | H |
| CH3 | 4-Cl-C6H4-CH2- | H | Cl | H | 6-Cl |
| CH3 | 4-CH3-C6H4-CH2- | H | Cl | Cl | H |
| CH3 | 4-CH3-C6H4-CH2- | H | Cl | H | 6-Cl |
| CH3 | 4-CH3-C6H4-CH2- | H | CH3 | CH3 | 6-CH3 |
| CH3 | 3-CF3-C6H4-CH2- | H | Cl | Cl | H |
| CH3 | 3-CF3-C6H4-CH2- | H | Cl | H | 6-Cl |
| CH3 | 3-CF3-C6H4-CH2- | H | CH3 | CH3 | 6-CH3 |
| CH3 | C6H5-CH2- | H | Cl | Cl | H |
| CH3 | C6H5-CH2- | H | Cl | H | 6-Cl |
| CH3 | 2-Cl-C6H4-CH2- | H | Cl | Cl | H |
| CH3 | 2-Cl-C6H4-CH2- | H | Cl | H | 6-Cl |
| CH3 | C6H5-CH2- | (CH3)3C-C(=O)- | Cl | Cl | H |
| CH3 | C6H5-CH2- | (CH3)3C-C(=O)- | H | Cl | 3-Cl |
| CH3 | C6H5-CH2- | (CH3)3C-C(=O)- | Cl | H | 6-Cl |
| CH3 | C6H5-CH2- | (CH3)3C-C(=O)- | Cl | CF3 | 6-Cl |
| CH3 | C6H5-CH2- | (CH3)3C-C(=O)- | CH3 | CH3 | 6-CH |
| CH3 | 2-Cl-C6H4-CH2- | (CH3)3C-C(=O)- | Cl | Cl | H |
| CH3 | 2-Cl-C6H4-CH2- | (CH3)3C-C(=O)- | H | Cl | 3-Cl |
| CH3 | 2-Cl-C6H4-CH2- | (CH3)3C-C(=O)- | Cl | H | 6-Cl |
| CH3 | 2-Cl-C6H4-CH2- | (CH3)3C-C(=O)- | Cl | CF3 | 6-Cl |
| CH3 | 3-Cl-C6H4-CH2- | (CH3)3C-C(=O)- | Cl | Cl | H |
| CH3 | 3-Cl-C6H4-CH2- | (CH3)3C-C(=O)- | H | Cl | 3-Cl |
| CH3 | 3-Cl-C6H4-CH2- | (CH3)3C-C(=O)- | Cl | H | 6-Cl |
| CH3 | 3-Cl-C6H4-CH2- | (CH3)3C-C(=O)- | Cl | CF3 | 6-Cl |

TABLE 1-continued (I)

Structure: B-CH(R-O)-C(=C(A-N)-C(=O)-)- aryl with X, Y, Zn substituents

| A | B | R | X | Y | Zn |
|---|---|---|---|---|---|
| CH₃ | 4-Cl-C₆H₄-CH₂- | (CH₃)₃C-C(=O)- | Cl | Cl | H |
| CH₃ | 4-Cl-C₆H₄-CH₂- | (CH₃)₃C-C(=O)- | H | Cl | 3-Cl |
| CH₃ | 4-Cl-C₆H₄-CH₂- | (CH₃)₃C-C(=O)- | Cl | H | 6-Cl |
| CH₃ | 4-Cl-C₆H₄-CH₂- | (CH₃)₃C-C(=O)- | Cl | CF₃ | 6-Cl |
| CH₃ | 4-CH₃-C₆H₄-CH₂- | -C(CH₃)₃ | Cl | Cl | H |
| CH₃ | 4-CH₃-C₆H₄-CH₂- | -C(CH₃)₃ | H | Cl | 3-Cl |
| CH₃ | 4-CH₃-C₆H₄-CH₂- | -C(CH₃)₃ | Cl | H | 6-Cl |
| CH₃ | 4-CH₃-C₆H₄-CH₂- | -C(CH₃)₃ | Cl | CF₃ | 6-Cl |
| CH₃ | 4-CH₃-C₆H₄-CH₂- | -C(CH₃)₃ | CH₃ | CH₃ | 6-CH₃ |
| CH₃ | 3-CF₃-C₆H₄-CH₂- | -C(CH₃)₃ | Cl | Cl | H |
| CH₃ | 3-CF₃-C₆H₄-CH₂- | -C(CH₃)₃ | H | Cl | 3-Cl |
| CH₃ | 3-CF₃-C₆H₄-CH₂- | -C(CH₃)₃ | Cl | H | 6-Cl |
| CH₃ | 3-CF₃-C₆H₄-CH₂- | -C(CH₃)₃ | Cl | CF₃ | 6-Cl |
| CH₃ | 3-CF₃-C₆H₄-CH₂- | -C(CH₃)₃ | CH₃ | CH₃ | 6-CH₃ |
| CH₃ | 4-CH₃-C₆H₄- | (CH₃)₃C-C(=O)- | Cl | Cl | H |
| CH₃ | 4-CH₃-C₆H₄- | (CH₃)₃C-C(=O)- | H | Cl | 3-Cl |
| CH₃ | 4-CH₃-C₆H₄- | (CH₃)₃C-C(=O)- | Cl | H | 6-Cl |
| CH₃ | 4-CH₃-C₆H₄- | (CH₃)₃C-C(=O)- | Cl | CF₃ | 6-Cl |
| CH₃ | 4-CH₃-C₆H₄- | (CH₃)₃C-C(=O)- | CH₃ | CH₃ | 6-CH₃ |
| CH₃ | 4-CH₃O-C₆H₄- | (CH₃)₃C-C(=O)- | Cl | Cl | H |
| CH₃ | 4-CH₃O-C₆H₄- | (CH₃)₃C-C(=O)- | H | Cl | 3-Cl |
| CH₃ | 4-CH₃O-C₆H₄- | (CH₃)₃C-C(=O)- | Cl | H | 6-Cl |
| CH₃ | 4-CH₃O-C₆H₄- | (CH₃)₃C-C(=O)- | Cl | CF₃ | 6-Cl |
| CH₃ | 4-CH₃O-C₆H₄- | (CH₃)₃C-C(=O)- | CH₃ | CH₃ | 6-CH₃ |
| CH₃ | C₆H₅- | (CH₃)₃C-C(=O)- | Cl | Cl | H |
| CH₃ | C₆H₅- | (CH₃)₃C-C(=O)- | H | Cl | 3-Cl |
| CH₃ | C₆H₅- | (CH₃)₃C-C(=O)- | Cl | H | 6-Cl |
| CH₃ | C₆H₅- | (CH₃)₃C-C(=O)- | Cl | CF₃ | 6-Cl |
| CH₃ | 2-Cl-C₆H₄- | (CH₃)₃C-C(=O)- | Cl | Cl | H |
| CH₃ | 2-Cl-C₆H₄- | (CH₃)₃C-C(=O)- | H | Cl | 3-Cl |
| CH₃ | 2-Cl-C₆H₄- | (CH₃)₃C-C(=O)- | Cl | H | 6-Cl |
| CH₃ | 2-Cl-C₆H₄- | (CH₃)₃C-C(=O)- | Cl | CF₃ | 6-Cl |
| CH₃ | 3-Cl-C₆H₄- | (CH₃)₃C-C(=O)- | Cl | Cl | H |

TABLE 1-continued (I)

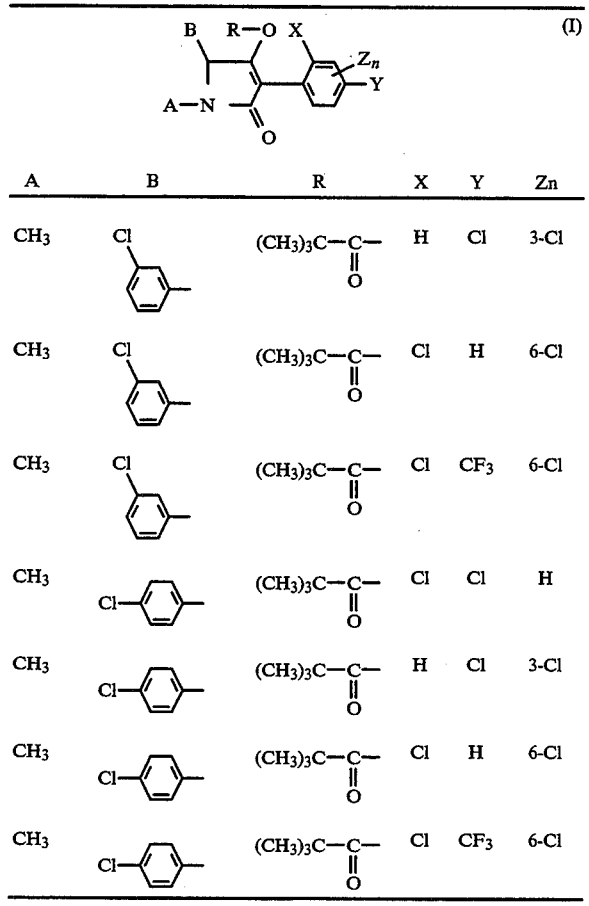

| A | B | R | X | Y | Zn |
|---|---|---|---|---|---|
| CH₃ | 3-Cl-C₆H₄ | (CH₃)₃C—CO— | H | Cl | 3-Cl |
| CH₃ | 3-Cl-C₆H₄ | (CH₃)₃C—CO— | Cl | H | 6-Cl |
| CH₃ | 3-Cl-C₆H₄ | (CH₃)₃C—CO— | Cl | CF₃ | 6-Cl |
| CH₃ | 4-Cl-C₆H₄ | (CH₃)₃C—CO— | Cl | Cl | H |
| CH₃ | 4-Cl-C₆H₄ | (CH₃)₃C—CO— | H | Cl | 3-Cl |
| CH₃ | 4-Cl-C₆H₄ | (CH₃)₃C—CO— | Cl | H | 6-Cl |
| CH₃ | 4-Cl-C₆H₄ | (CH₃)₃C—CO— | Cl | CF₃ | 6-Cl |

If, according to process (A), N-2,6-dichlorophenylacetyl-N-methyl-phenylalanine ethyl ester is used, the course of the process according to the invention can be described by the following equation:

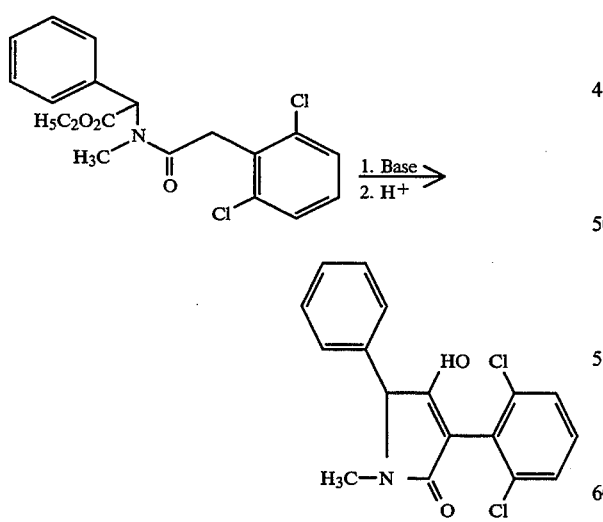

If, according to process (B) (variant α), 3-(2,4,6-trimethylphenyl)-1-isopropyl-5-benzyl-pyrrolidine-2,4-dione and pivaloyl chloride are used as starting substance, the course of the process according to the invention can be described by the following equation:

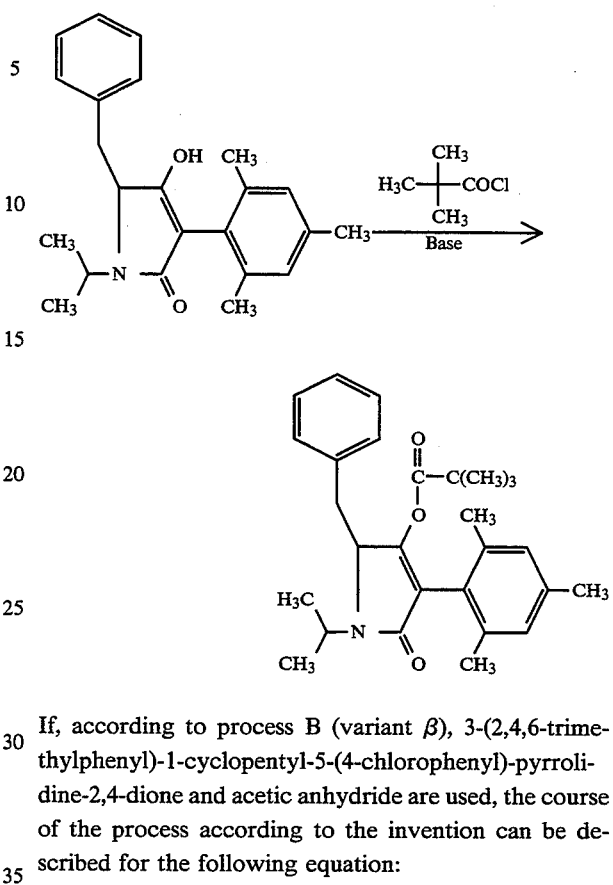

If, according to process B (variant β), 3-(2,4,6-trimethylphenyl)-1-cyclopentyl-5-(4-chlorophenyl)-pyrrolidine-2,4-dione and acetic anhydride are used, the course of the process according to the invention can be described for the following equation:

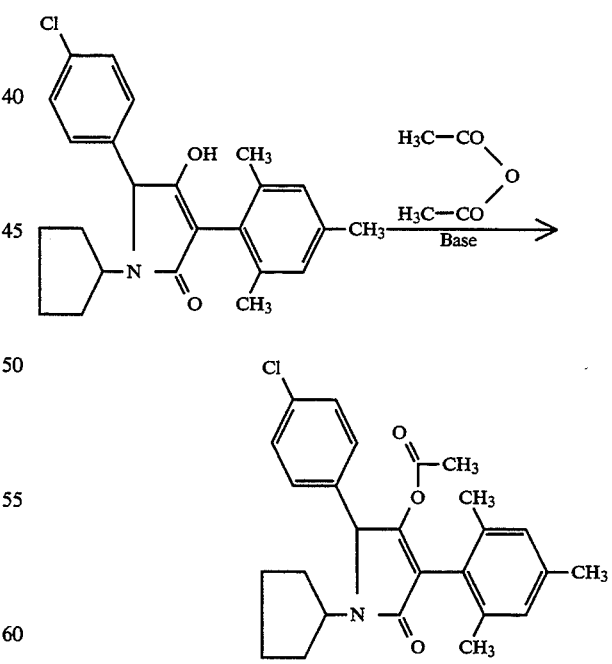

If, according to process C, 3-(2,4-6-trimethylphenyl)-1-methoxyethyl-5-phenyl-pyrrolidine-2,4-dione and ethoxyethyl chloroformate are used, the course of the process according to the invention can be described by the following equation:

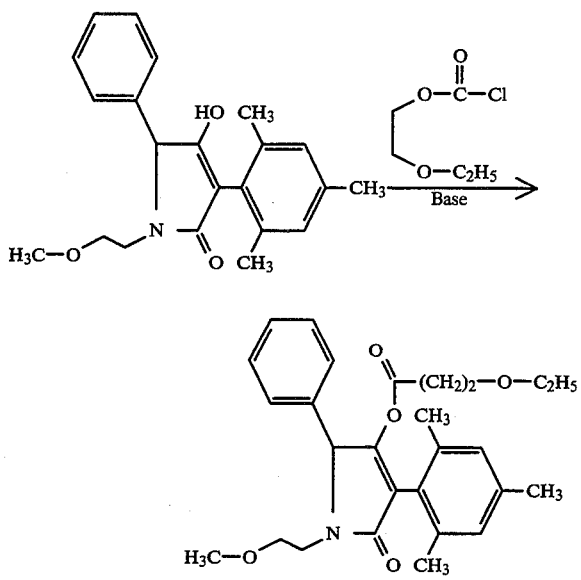

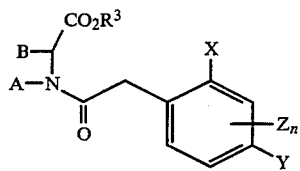

Some of the compounds of the formula (II)

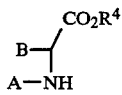

in which

A, B, X, Y, Z, n and $R^3$ have the abovementioned meaning and which are required as starting substances in the above process (A), are known or can be prepared in a simple manner by methods known in principle. For example, acyl-amino acid esters of the formula (II) are obtained when a) amino acid esters of the formula (VI)

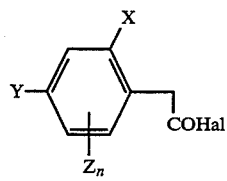 (VI)

in which $R^4$ represents hydrogen (VIa) and alkyl (VIb), and

A and B have the abovementioned meaning are acylated with phenylacetyl halides of the formula (VII)

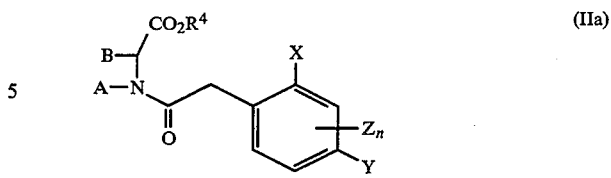 (VII)

in which

X, Y, Z and n have the abovementioned meaning and Hal represents chlorine or bromine (Chem. Reviews 52 237–416 (1953));

or when acylamino acids of the formula (IIa)

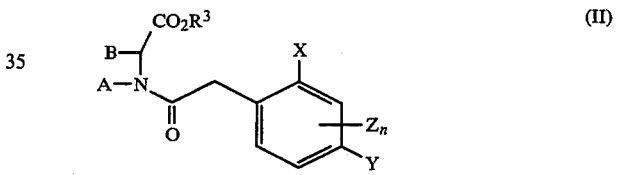 (IIa)

in which

A, B, X, Y, Z and n have the abovementioned meaning and $R^4$ represents hydrogen, are esterified (Chem. Ind. (London) 1568 (1968)).

Compounds of the formula (IIa) can be obtained, for example, from the phenylacetyl halides of the formula (VII) and amino acids of the formula (VIa) by the method of Schotten-Baumann (Organikum, 9th edition, 446 (1970) VEB Deutscher Verlag der Wisenschaften, Berlin).

Compounds of the formula VI in which A, B and $R^4$ have the abovementioned meaning can be obtained by processes known from the literature, for example from α-halogenocarboxylic acids or halogenocarboxylic esters and amines (Advanced Organic Chemistry, J. March p. 377, McGraw-Hill Inc. 1977) or by reacting aldehydes with cyanide and amines by the Strecker synthesis (cf., for example, Org. Synth. 22 24 (1942) and Org. Synth. Coll. Vol. III, 705).

The following compounds of the formula (II) may be mentioned by way of examples:

(II)

2-phenyl-N-(2,4-dichlorophenyl-acetyl)-sarcosine ethyl ester 2-phenyl-N-(3,4-dichlorophenyl-acetyl)-sarcosine ethyl ester 2-phenyl-N-(2,6-dichlorophenyl-acetyl)-sarcosine ethyl ester 2-(2-chlorophenyl)-N-(2,4-dichlorophenyl-acetyl)-sarcosine ethyl ester 2-(2-chlorophenyl)-N-(3,4-dichlorophenyl-acetyl)-sarcosine ethyl ester 2-(2 -chlorophenyl)-N-(2,6-dichlorophenyl-acetyl)-sarcosine ethyl ester 2-(3-chlorophenyl)-N-(2,4-dichlorophenyl-acetyl)-sarcosine ethyl ester 2-(3-chlorophenyl)-N-(3,4-dichlorophenyl-acetyl)-sarcosine ethyl ester 2-(3-chlorophenyl)-N-(2,6-dichlorophenyl-acetyl)-sarcosine ethyl ester 2-phenyl-N-(2,4,6-trimethylphenyl-acetyl)-sarcosine ethyl ester 2-(2-chlorophenyl)-N-(2,4,6-trimethylphenyl-acetyl)-sarcosine ethyl ester 2-(3-chlorophenyl)-N-(2,4,6-trimethylphenyl-acetyl)-sarcosine ethyl ester 2-(4-chlorophenyl)-N-(2,4,6-trimethylphenyl-acetyl)-sarcosine ethyl ester 2-(4-methylphenyl)-N-(2,4,6-trimethylphenyl-acetyl)-sarcosine ethyl ester 2-(4-chlorophenyl)-N-(2,4-dichlorophenyl-acetyl)-sarcosine ethyl ester
2-(4-chlorophenyl)-N-(3,4-dichlorophenyl-acetyl)-sarcosine ethyl ester
2-(4-chlorophenyl)-N-(2,6-dichlorophenyl-acetyl)-sarcosine ethyl ester
2-(4-methylphenyl)-N-(2,4-dichlorophenyl-acetyl)-sarcosine ethyl ester
2-(4-methylphenyl)-N-(3,4-dichlorophenyl-acetyl)-sarcosine ethyl ester
2-(4-methylphenyl)-N-(2,6-dichlorophenyl-acetyl)-sarcosine ethyl ester
2-(4-methoxyphenyl)-N-(2,4-dichlorophenyl-acetyl)-sarcosine ethyl ester
2-(4-methoxyphenyl)-N-(3,4-dichlorophenyl-acetyl)-sarcosine ethyl ester
2-(4-methoxyphenyl)-N-(2,6-dichlorophenyl-acetyl)-sarcosine ethyl ester
2-(4-methoxyphenyl)-N-(2,4,6-trimethylphenyl-acetyl)-sarcosine ethyl ester
2-(4-chlorophenyl)-N-(2,6-dichlorophenyl-4-trifluoromethyl-acetyl)-sarcosine ethyl ester
2-(4-methylphenyl)-N-(2,6-dichlorophenyl-4-trifluoromethyl-acetyl)-sarcosine ethyl ester
2-(4-methylphenyl)-N-(2,6-dichlorophenyl-4-trifluoromethyl-acetyl)-sarcosine ethyl ester
2-phenyl-N-(2,6-dichlorophenyl-4-trifluoromethyl-acetyl)-sarcosine ethyl ester
2-(2-chlorophenyl)-N-(2,6-dichlorophenyl-4-trifluoromethyl-acetyl)-sarcosine ethyl ester
2-(3-chlorophenyl)-N-(2,6-dichlorophenyl-4-trifluoromethyl-acetyl)-sarcosine ethyl ester
2-benzyl-N-(2,4-dichlorophenyl-acetyl)-sarcosine ethyl ester
2-benzyl-N-(3,4-dichlorophenyl-acetyl)-sarcosine ethyl ester
2-benzyl-N-(2,6-dichlorophenyl-acetyl)-sarcosine ethyl ester
2-(2-chlorobenzyl)-N-(2,4-dichlorophenyl-acetyl)-sarcosine ethyl ester
2-(2-chlorobenzyl)-N-(3,4-dichlorophenyl-acetyl)-sarcosine ethyl ester
2-(2-chlorobenzyl)-N-(2,6-dichlorophenyl-acetyl)-sarcosine ethyl ester
2-(3-chlorobenzyl)-N-(2,4-dichlorophenyl-acetyl)-sarcosine ethyl ester
2-(3-chlorobenzyl)-N-(3,4-dichlorophenyl-acetyl)-sarcosine ethyl ester
2-(3-chlorobenzyl)-N-(2,6-dichlorophenyl-acetyl)-sarcosine ethyl ester
2-benzyl-N-(2,4,6-trimethylphenyl-acetyl)-sarcosine ethyl ester
2-(2-chlorobenzyl)-N-(2,4,6-trimethylphenyl-acetyl)-sarcosine ethyl ester
2-(3-chlorobenzyl)-N-(2,4,6-trimethylphenyl-acetyl)-sarcosine ethyl ester
2-(4-chlorobenzyl)-N-(2,4,6-trimethylphenyl-acetyl)-sarcosine ethyl ester
2-(4-methylbenzyl)-N-(2,4,6-trimethylphenyl-acetyl)-sarcosine ethyl ester
2-(4-chlorobenzyl)-N-(2,4-dichlorophenyl-acetyl)-sarcosine ethyl ester
2-(4-chlorobenzyl)-N-(3,4-dichlorophenyl-acetyl)-sarcosine ethyl ester
2-(4-chlorobenzyl)-N-(2,6-dichlorophenyl-acetyl)-sarcosine ethyl ester
2-(4-methylbenzyl)-N-(2,4-dichlorophenyl-acetyl)-sarcosine ethyl ester
2-(4-methylbenzyl)-N-(3,4-dichlorophenyl-acetyl)-sarcosine ethyl ester
2-(4-methylbenzyl)-N-(2,6-dichlorophenyl-acetyl)-sarcosine ethyl ester
2-(3-trifluoromethylbenzyl)-N-(2,4-dichlorophenyl-acetyl)-sarcosine ethyl ester
2-(3-trifluoromethylbenzyl)-N-(3,4-dichlorophenyl-acetyl)-sarcosine ethyl ester
2-(3-trifluoromethylbenzyl)-N-(2,6-dichlorophenyl-acetyl)-sarcosine ethyl ester
2-benzyl-N-(2,6-dichlorophenyl-4-trifluoromethyl-acetyl)-sarcosine ethyl ester
2-(2-chlorobenzyl)-N-(2,6-dichlorophenyl-4-trifluoromethyl-acetyl)-sarcosine ethyl ester
2-(3-chlorobenzyl)-N-(2,6-dichlorophenyl-4-trifluoromethyl-acetyl)-sarcosine ethyl ester
2-(4-chlorobenzyl)-N-(2,6-dichlorophenyl-4-trifluoromethyl-acetyl)-sarcosine ethyl ester
2-(4-methylbenzyl)-N-(2,6-dichlorophenyl-4-trifluoromethyl-acetyl)-sarcosine ethyl ester
5-(3-trifluoromethylbenzyl)-N-(2,6-dichlorophenyl-4-trifluoromethyl-acetyl)-sarcosine ethyl ester Process (A) is characterised in that compounds of the formula (II) in which A, B, X, Y, Z, n and $R^3$ have the abovementioned meaning are subjected to an intramolecular condensation reaction in the presence of bases.

Diluents which can be employed in process (A) according to the invention are all customary inert organic solvents. The following can preferably be used: hydrocarbons such as toluene and xylene, furthermore ethers such as dibutyl ether, tetrahydrofuran, dioxane, glylcol dimethyl ether and diglycol dimethyl ether, moreover polar solvents such as dimethyl sulphoxide, sulpholane, dimethylformamide and N-methyl-pyrrolidone.

Deprotonating agents which can be employed when carrying out process (A) according to the invention are all customary proton acceptors. The following can preferably be used: alkali metal oxides, alkali metal hydroxides, alkali metal carbonates, alkaline earth metal oxides, alkaline earth metal hydroxides and alkaline earth metal carbonates, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 or TDA 1. Other compounds which can be employed are alkali metal amides, alkali metal hydrides, alkaline earth metal amides and alkaline earth metal hydrides such as sodium amide, sodium hydride and calcium hydride, and moreover also alkali metal alkoxides such as sodium methoxide, sodium methoxide and potassium tert.-butoxide.

When carrying out process (A) according to the invention, the reaction temperatures can be varied within a substantial range. In general, the process is carried out at temperatures between 0° C. and 250° C., preferably between 50° C. and 150° C.

In general, process (A) according to the invention is carried out under atmospheric pressure.

Adogen 464=Methyltrialkyl ($C_8$–$C_{10}$)ammonium chloride

TDA 1=Tris-(methoxyethoxyethyl)-amine

When carrying out process (A) according to the invention, the reactants of the formulae (II) and the deprotonating bases are generally employed in approximately equimolar amounts. However, it is also possible to use one or the other component in a larger excess (up to 3 mol).

Process (Bα) is characterised in that compounds of the formula (Ia) are reacted with carboxylic acid halides of the formula (III).

When the acid halides are used, diluents which can be employed in process (Bα) according to the invention are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers, such as diethyl ether, tetrahydrofuran and dioxane, furthermore carboxylic acid esters such as ethyl acetate, and also strongly polar solvents such as dimethyl sulphoxide and sulpholane. If the acid halide is sufficiently stable to hydrolysis, the reaction can also be carried out in the presence of water.

If the corresponding carboxylic acid halides are used, suitable acid-binding agents in the reaction of process (Bα) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides such as magnesium oxide and calcium oxide, moreover alkali metal carbonates and alkaline earth metal carbonates such as sodium carbonate, potassium carbonate and calcium carbonate.

Even when carboxylic acid halides are used, the reaction temperatures in process (Bα) according to the invention can also be varied within a substantial range. In general, the process is carried out at temperatures between −20° C. and +150° C., preferably between 0° C. and 100° C.

When carrying out process (Bα) according to the invention, the starting substances of the formula (Ia) and the carboxylic acid halide of the formula (III) are generally used in approximately equivalent amounts. However, it is also possible to employ the carboxylic anhydride in a larger excess (up to 5 mol). work-up is carried out by customary methods.

Process (Bβ) is characterised in that compounds of the formula (Ia) are reacted with carboxylic anhydrides of the formula (IV).

If, in process (Bβ) according to the invention, carboxylic anhydrides are used as reactant of the formula (Iv), the diluents which can be used are preferably those diluents which are also preferably suitable when acid halides are used. Besides, an excess of the carboxylic acid hydride employed can also simultaneously act as the diluent.

Even when using carboxylic anhydrides, the reaction temperatures in process (Bβ) according to the invention can also be varied within a substantial range. In general, the process is carried out at temperatures between −20° C. and +150° C., preferably between 0° C. and 100° C.

When carrying out the process according to the invention, the starting substances of the formula (Ia) and the carboxylic anhydride of the formula (IV) are generally used in approximately equivalent amounts. However, it is also possible to employ the carboxylic anhydride in a larger excess (up to 5 mol). Work-up is carried out by customary methods.

In general, the procedure is such that diluent and excess carboxylic anhydride as well as the carboxylic acid formed are removed by distillation or by washing with an organic solvent or with water.

Process (C) is characterised in that compounds of the formula (Ia) are reacted with chloroformic esters of the formula (V).

If the corresponding chloroformic esters are used, suitable acid-binding agents in the reaction by process (C) according to the invention are all customary acid acceptors. The following can preferably be used: tertiary amines such as triethylamine, pyridine, DABCO, DBC, DBA, Hünig base and N,N-dimethyl-aniline, furthermore alkaline earth metal oxides such as magnesium oxide and calcium oxide, moreover alkali metal carbonates and alkaline earth metal carbonates such as sodium carbonate, potassium carbonate and calcium carbonate.

When the chloroformic esters are used, diluents which can be employed in process (C) according to the invention are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, furthermore carboxylic acid esters such as ethyl acetate, and also strongly polar solvents such as dimethyl sulphoxide and sulpholane.

When using the chloroformic esters as carboxylic acid derivatives of the formula (V), the reaction temperatures when carrying out process (C) according to the invention can be varied within a substantial range. If the process is carried out in the presence of a diluent and of an acid-binding agent, the reaction temperatures are generally between −20° C. and +100° C., preferably between 0° C. and 50° C.

Process (C) according to the invention is generally carried out under atmospheric pressure.

When carrying out process (C) according to the invention, the starting substances of the formula (Ia) and the corresponding (chloroformic ester of the formula (V) are generally used in approximately equivalent amounts. However, it is also possible to employ one or the other component in a larger excess (up to 2 mol). Work-up is then carried out by customary methods. In general, the procedure is such that precipitated salts are removed and the reaction mixture which remains is concentrated by stripping off the diluent.

The active compounds according to the invention exhibit a powerful action against pests and can be employed in practice for combating undesirable harmful organisms. The active compounds are suitable for use as plant protection agents, in particular as insecticides, acaricides and fungicides.

The active compounds according to the invention are suitable for combating animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp.

From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundins, Macrosiphum avenae,* Myzus spp., *Phorodon humuli, Rhopalosiphum pad,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrostis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilu spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharanois* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Cacus oleae* and *Tipula paludosa*.

From the order of the Siphonaptera, for example, *Xenopsylla cheopis* and Ceratophyllus spp. From the order of the Arachnida, for example, *Scorpio maurus* and *Latrodectus mactans*.

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Globedera ssp., Meloidogyne spp., Aphelenchoides spp., Longidorus spp., Xiphinema spp. and Trichodorus spp.

The active compounds according to the invention are distinguished, in particular, by a powerful insecticidal and acaricidal activity.

They can be employed with particularly good success for combating insects which damage plants such as, for example, against the caterpillars of the cabbage moth (*Plutella maculipennis*) or against mites which damage plants such as, for example, against the greenhouse bred spider mite or the two-spotted spider mite (*Tetranychus urticae*).

Moreover, the active compounds according to the invention are suitable as fungicidal agents in plant protection. They are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Pythium species, such as, for example, *Phythium ultimum;*

Phytophthora species, such as, for example, *Phytophthora infestans;*

Pseudoperonospora species, such as, for example, *Psuedoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita*;

Tilletia species, such as, for example, *Tilletia caries*;

Ustilago species, such as, for example, *Ustilago nuda* or *Ustilago avanea*;

Pellicularia species, such as, for example, *Pellicularia sasakii*;

Pyricularia species, such as, for example, *Pyricularia oryaze*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicase* and

Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for protectively combating Erysiphebarley species.

Moreover, the active compounds according to the invention also exhibit a fungicidal action against *Pyricularia oryzae* on rice.

To a certain extent, the compounds of the formula (I) furthermore also exhibit a herbicidal action.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The compounds of the formula (I) according to the invention exhibit antimicrobial, in particular powerful antibacterial and antimycotic, actions. They have a very broad antimycotic spectrum of action, in particular against dermatophytes and yeasts as well as biphasic fungi, for example against Candida species such as *Candida albicans,* Epidermophyton species such as *Epidermophyton floccosum,* Aspergillus species such as *Aspergillus niger* and *Aspergillus fumigatus,* Trichophyton species such as *Trichophyton mentagrophytes,* Microsporon species such as *Microsporon felineum* as well as Torulopsis species such as *Torulopsis glabrata.* However, this list of microorganisms in no way represents a limitation of the microorganisms which can be combated, but has only illustrating character.

Examples of indication in human medicine which may be mentioned are, for example: Dermatomycoses and Systemicmycoses caused by *Trichophyton mentagrophytes* and other Trichophyton species, Microsporon species as well as *Epidermophyton floccosum,* yeasts and biphasic fungi, as well as module.

The following may be mentioned by way of example as fields of indication in verterinary medicine; all Dermatomycoses and Systemicmyoses, in particular those caused by the abovementioned pathogens.

The present invention includes pharmaceutical preparations which contain one or more active compounds according to the invention or which consist of one or more active compounds according to the invention in addition to non-toxic, inert, pharmaceutically suitable excipients.

The present invention also includes pharmaceutical preparations in dosage units. This means that the preparations are in the form of individual portions, for example tablets, coated tablets, capsules, pills, suppositories and ampoules, whose active compound content corresponds to a fraction or a multiple of an individual dose. The dosage units may contain, for example, 1, 2, 3 or 4 individual doses or $\frac{1}{2}$, $\frac{3}{4}$ or $\frac{1}{4}$ of an individual dose. An individual dose preferably contains the amount of active compound which is administered in one application and which usually corresponds to a whole, a half, a third or a quarter of a daily dose.

Non-toxic, inert, pharmaceutically suitable excipients are taken to mean solid, semi-solid or liquid diluents, fillers or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders and sprays.

Tablets, coated tablets, capsules, pills and granules may contain the active compound(s) in addition to the customary excipients, such as (a) fillers and extenders, for example starches, lactose, sucrose, glucose, mannitol and silica, (b) binders, for example carboxymethylcellulose, alginates, gelantin, polyvinylpyrrolidone, (c) humectants, for example glycerol, (d) disintegrants, for example agar-agar, calcium carbonate and sodium bicarbonate, (e) dissolution retarders, for example paraffin and (f) absorption accelerators, for example quaternary ammonium compounds, (g) wetting agents, for example cetyl alcohol, glycerol monostearate, (h) adsorbants, for example kaolin and bentonite and (i) lubricants, for example talc, calcium stearate and magnesium stearate and solid polyethylene glycols or mixtures of the substances mentioned under (a) to (i).

The tablets, coated tablets, capsules, pills and granules may be provided with the customary coatings and covers containing, if appropriate, opacifying agents, and can be composed such that they release the active compound(s), only or preferably in a certain part of the intestinal tract, if appropriate with a delay, it being possible, for example, to use polymeric substances and waxes as embedding materials.

If appropriate, the active compound(s) may also be present in micro-encapsulated form together with one or more of the abovementioned excipients.

Suppositories may contain the customary water-soluble or water-insoluble excipients, for example polyethylene glycols, fats, for example cocoa fat and higher esters (for example $C_{14}$-alcohol with $C_{16}$-fatty acid) or mixtures of these substances in addition to the active compound(s).

Ointments, pastes, creams and gels may contain the customary excipients, for example animal and vegetable fats, waxes, paraffins, starch, tragacanth, cellulose derivatives, polyethylene glycols, silicones, bentonites, silica, talc and zinc oxide or mixtures of these substances in addition to the active compound(s).

Powders and sprays may contain the customary excipients, for example lactose, talc, silica, aluminium hydroxide, calcium silicate and polyamide powder or mixtures of these substances in addition to the active compound(s), and sprays may additionally contain the customary propellants, for example chlorofluorohydrocarbons.

Solutions and emulsions may contain the customary excipients, such as solvents, dissolution retarders and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerol formal, tetrahydrofurfuryl alcohol, polyethylene glycols and fatty acid esters of sorbitan or mixtures of these substances in addition to the active compounds(s).

For parenteral administration, the solutions and emulsions may also be present in sterile and blood-isotonic form.

Suspensions may contain the customary excipients, such as liquid diluents, for example water, ethyl alcohol, propyl alcohol, suspending agents, for example ethoxylated isostearyl alcohols, polyoxyethylene sorbitol and sorbitan esters, microcrystalline cellulose, aluminium metahydroxide, bentonite, agar-agar and tragacanth or mixtures of these substances in addition to the active compound(s).

The formulation forms mentioned may also contain colorants, preservatives and also odour-improving and flavour-improving additives, for example peppermint oil and eucalyptus oil and sweeteners, for example saccharin.

The therapeutically active compounds should preferably be present in the abovementioned pharmaceutical preparations in a concentration of about 0.1 to 99.5, preferably of about 0.5 to 95% by weight, of the total mixture.

The abovementioned pharmaceutical preparations may also contain further pharmaceutical active compounds in addition to the compounds according to the invention.

The preparation of the abovementioned pharmaceutical preparations takes place in a customary manner by known methods, for example by mixing the active compound(s) with the excipient(s).

The present invention also includes the use of the active compounds according to the invention, and the use of pharmaceutical preparations which contain one or more active compounds according to the invention, in human medicine and veterinary medicine for preventing, alleviating and/or curing the abovementioned diseases.

The active compounds or the pharmaceutical preparations can be administered locally, orally, parenterally, intraperitoneally and/or rectally, preferably parenterally, in particular intravenously.

In general, it has proved advantageous in both human and veterinary medicine to administer the active compound(s) according to the invention in total amounts of approximately 2.5 to approximately 200, preferably 5 to 150, mg/kg of bodyweight per 24 hours, if appropriate in the form of several individual doses, for attaining the desired results.

In the case of oral administrations, the active compounds according to the invention are administered in total amounts of approximately 2.5 to approximately 200, preferably 5 to 150, mg/kg of bodyweight per 24 hours, and in the case of parenteral application in total amounts of approximately 2.5 to approximately 50, preferably 1 to 25, mg/kg of bodyweight per 24 hours.

However, it may be necessary to depart from the dosages mentioned, namely depending on the nature and the bodyweight of the subject to be treated, the nature and severity of the disease, the nature of the preparation and the administration of the medicament, and the period of time or interval within which the application takes place. Thus, in some cases it may suffice to manage with less than the abovementioned amount of active compound, while in other cases the abovementioned amount of active compound must be exceeded. The optimum dosage required in each case and type of administration of the active compounds can easily be established by any person skilled in the art on the basis of his expert knowledge.

PREPARATION EXAMPLES

EXAMPLE 1

(Process A)

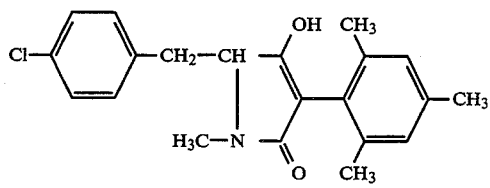

To a boiling solution of 120 ml of absolute toluene and 7.5 g (0.25 mol) of sodium hydride there are added dropwise 79.9 g (0.199 mol) of 2-(4-chlorobenzyl)-N-(2,4,6-trimethylphenylacetyl)-sarcosine ethyl ester in 200 ml of absolute toluene, and the batch is refluxed while being monitored by thin-layer chromatography. When the reaction is complete, ethanol is added dropwise, while cooling in an ice-bath, until no more hydrogen escapes. After the mixture has been evaporated under reduced pressure, the residue is taken up in water and the mixture is acidified with concentrated hydrochloric acid at 0° C. to 20° C. The precipitate is filtered off with suction and recrystallised from chloroform/n-hexane. 48.4 g (68.4% of Theory) of 5-(4-chlorobenzyl)-1-methyl-3-(2,4,6-trimethylphenyl)-pyrrolidine-2,4-dione of melting point >230° C. are obtained.

EXAMPLE 2

(Process Bα)

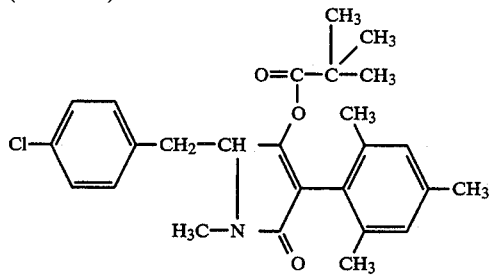

To a solution of 7.12 g (0.02 mol) of 5-(4-chlorobenzyl)-1-methyl-3-(2,4,6-trimethylphenyl)-pyrrolidine-2,4-dione in 70 ml of methyl t-butyl ether and 3.4 ml of ethyldiisopropylamine there are added dropwise at 0° C. to 10° C. 2.52 ml of pivaloyl chloride in 5 ml of methyl t-butyl ether, and the batch is stirred at room temperature. When the reaction is complete (monitored by thin-layer chromatography), the precipitate which has separated out is filtered off with suction and rinsed with methyl t-butyl ether, and the filtrate is concentrated. Purification by column chromatography (mobile phase: cyclohexane/ethyl acetate 1:1 on silica gel) gives 7.4 g (84% of theory) of 4-t-butyryl-5-(4-chlorobenzyl)-1-methyl-3-(2,4,6-trimethylphenyl)-pyrrolidine-2,4-dione as an oil.

The end products of the formula (I)

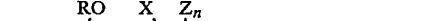

which are listed below in Table 2 are obtained analogously to Example 1 and 2, while taking into consideration the details given in the description of the processes according to the invention:

TABLE 2

| Ex. No. | A | B | R | X | Y | $Z_n$ | M.p. °C. |
|---|---|---|---|---|---|---|---|
| 3 | $CH_3$ |  | H | H | Cl | 3-Cl | 210-212 |

TABLE 2-continued

| Ex. No. | A | B | R | X | Y | Zn | M.p. °C. |
|---|---|---|---|---|---|---|---|
| 4 | CH$_3$ | 3-Cl-C$_6$H$_4$ | H | Cl | CF$_3$ | 6-Cl | 240 |
| 5 | CH$_3$ | 3-Cl-C$_6$H$_4$ | H | CH$_3$ | CH$_3$ | 6-CH$_3$ | 228 |
| 6 | CH$_3$ | 4-Cl-C$_6$H$_4$ | H | H | Cl | 3-Cl | 191–193 |
| 7 | CH$_3$ | 4-Cl-C$_6$H$_4$ | H | Cl | CF$_3$ | 6-Cl | 144 |
| 8 | CH$_3$ | 4-Cl-C$_6$H$_4$ | H | CH$_3$ | CH$_3$ | 6-CH$_3$ | >230 |
| 9 | CH$_3$ | C$_6$H$_5$ | H | H | Cl | 3-Cl | 186–190 |
| 10 | CH$_3$ | C$_6$H$_5$ | H | Cl | CF$_3$ | 6-Cl | >260 |
| 11 | CH$_3$ | C$_6$H$_5$ | H | CH$_3$ | CH$_3$ | 6-CH$_3$ | 248 |
| 12 | CH$_3$ | 2-Cl-C$_6$H$_4$ | H | H | Cl | 3-Cl | 216–220 |
| 13 | CH$_3$ | 2-Cl-C$_6$H$_4$ | H | Cl | CF$_3$ | 6-Cl | 208 |
| 14 | CH$_3$ | 2-Cl-C$_6$H$_4$ | H | CH$_3$ | CH$_3$ | 6-CH$_3$ | >230 |
| 15 | CH$_3$ | 4-CH$_3$-C$_6$H$_4$ | H | H | Cl | 3-Cl | 212–217 |

TABLE 2-continued

| Ex. No. | A | B | R | X | Y | Zn | M.p. °C. |
|---|---|---|---|---|---|---|---|
| 16 | $CH_3$ | 4-$CH_3$-$C_6H_4$– | H | Cl | $CF_3$ | 6-Cl | 230 |
| 17 | $CH_3$ | 4-$CH_3$-$C_6H_4$– | H | $CH_3$ | $CH_3$ | 6-$CH_3$ | 228 |
| 18 | $CH_3$ | 4-$CH_3O$-$C_6H_4$– | H | H | Cl | 3-Cl | 195–197 |
| 19 | $CH_3$ | 4-$CH_3O$-$C_6H_4$– | H | Cl | $CF_3$ | 6-Cl | 180 |
| 20 | $CH_3$ | 4-$CH_3O$-$C_6H_4$– | H | $CH_3$ | $CH_3$ | 6-$CH_3$ | 228 |
| 21 | $CH_3$ | 3-Cl-$C_6H_4$-$CH_2$– | H | H | Cl | 3-Cl | 205 |
| 22 | $CH_3$ | 3-Cl-$C_6H_4$-$CH_2$– | H | Cl | $CF_3$ | 6-Cl | 203–210 |
| 23 | $CH_3$ | 3-Cl-$C_6H_4$-$CH_2$– | H | $CH_3$ | $CH_3$ | 6-$CH_3$ | 228 |
| 24 | $CH_3$ | 4-Cl-$C_6H_4$-$CH_2$– | H | H | Cl | 3-Cl | 220–225 |
| 25 | $CH_3$ | 4-Cl-$C_6H_4$-$CH_2$– | H | Cl | $CF_3$ | 6-Cl | 224–228 |
| 26 | $CH_3$ | 4-$CH_3$-$C_6H_4$-$CH_2$– | H | H | Cl | 3-Cl | 206 |
| 27 | $CH_3$ | 4-$CH_3$-$C_6H_4$-$CH_2$– | H | Cl | $CF_3$ | 6-Cl | 213–215 |

TABLE 2-continued

| Ex. No. | A | B | R | X | Y | Zn | M.p. °C. |
|---|---|---|---|---|---|---|---|
| 28 | CH$_3$ | 3-CF$_3$-C$_6$H$_4$-CH$_2$- | H | H | Cl | 3-Cl | 194–196 |
| 29 | CH$_3$ | 3-CF$_3$-C$_6$H$_4$-CH$_2$- | H | Cl | CF$_3$ | 6-Cl | 204–207 |
| 30 | CH$_3$ | C$_6$H$_5$-CH$_2$- | H | H | Cl | 3-Cl | 219 |
| 31 | CH$_3$ | C$_6$H$_5$-CH$_2$- | H | Cl | CF$_3$ | 6-Cl | 177–180 |
| 32 | CH$_3$ | C$_6$H$_5$-CH$_2$- | H | CH$_3$ | CH$_3$ | 6-CH$_3$ | 198 |
| 33 | CH$_3$ | 2-Cl-C$_6$H$_4$-CH$_2$- | H | H | Cl | 3-Cl | 164–166 |
| 34 | CH$_3$ | 2-Cl-C$_6$H$_4$-CH$_2$- | H | Cl | CF$_3$ | 6-Cl | 164–167 |
| 35 | CH$_3$ | 2-Cl-C$_6$H$_4$-CH$_2$- | H | CH$_3$ | CH$_3$ | 6-CH$_3$ | 161 |
| 36 | CH$_3$ | C$_6$H$_5$- | CH$_3$-C(O)- | H | Cl | 3-Cl | 92–94 |
| 37 | CH$_3$ | C$_6$H$_5$- | CH$_3$-C(O)- | Cl | CF$_3$ | 6-Cl | 98 |
| 38 | CH$_3$ | C$_6$H$_5$- | CH$_3$-C(O)- | CH$_3$ | CH$_3$ | 6-CH$_3$ | Oil |
| 39 | CH$_3$ | 2-Cl-C$_6$H$_4$- | CH$_3$-C(O)- | H | Cl | 3-CH$_3$ | 80–85 |

TABLE 2-continued

| Ex. No. | A | B | R | X | Y | Zn | M.p. °C. |
|---|---|---|---|---|---|---|---|
| 40 | CH$_3$ | 2-Cl-C$_6$H$_4$ | CH$_3$-C(=O)- | Cl | CF$_3$ | 6-Cl | 136 |
| 41 | CH$_3$ | 2-Cl-C$_6$H$_4$ | CH$_3$-C(=O)- | CH$_3$ | CH$_3$ | 6-CH$_3$ | 120 |
| 42 | CH$_3$ | 3-Cl-C$_6$H$_4$ | CH$_3$-C(=O)- | H | Cl | 3-Cl | 74–76 |
| 43 | CH$_3$ | 3-Cl-C$_6$H$_4$ | CH$_3$-C(=O)- | Cl | CF$_3$ | 6-Cl | 140 |
| 44 | CH$_3$ | 3-Cl-C$_6$H$_4$ | CH$_3$-C(=O)- | CH$_3$ | CH$_3$ | 6-CH$_3$ | Oil |
| 45 | CH$_3$ | 4-Cl-C$_6$H$_4$ | CH$_3$-C(=O)- | H | Cl | 3-Cl | 105–108 |
| 46 | CH$_3$ | 4-Cl-C$_6$H$_4$ | CH$_3$-C(=O)- | Cl | CF$_3$ | 6-Cl | 134 |
| 47 | CH$_3$ | 4-Cl-C$_6$H$_4$ | CH$_3$-C(=O)- | CH$_3$ | CH$_3$ | 6-CH$_3$ | 118 |
| 48 | CH$_3$ | 4-CH$_3$-C$_6$H$_4$ | CH$_3$-C(=O)- | H | Cl | 3-Cl | 98–100 |
| 49 | CH$_3$ | 4-CH$_3$-C$_6$H$_4$ | CH$_3$-C(=O)- | Cl | CF$_3$ | 6-Cl | Oil |
| 50 | CH$_3$ | 4-CH$_3$O-C$_6$H$_4$ | CH$_3$-C(=O)- | H | Cl | 3-Cl | 78–80 |
| 51 | CH$_3$ | 4-CH$_3$O-C$_6$H$_4$ | CH$_3$-C(=O)- | Cl | CF$_3$ | 6-Cl | 150 |

TABLE 2-continued

| Ex. No. | A | B | R | X | Y | Zn | M.p. °C. |
|---|---|---|---|---|---|---|---|
| 52 | CH$_3$ | 3-Cl-phenyl | (CH$_3$)$_3$C—C(=O)— | CH$_3$ | CH$_3$ | 6-CH$_3$ | Oil |
| 53 | CH$_3$ | 4-Cl-phenyl | (CH$_3$)$_3$C—C(=O)— | CH$_3$ | CH$_3$ | 6-CH$_3$ | 98 |
| 54 | CH$_3$ | phenyl | (CH$_3$)$_3$C—C(=O)— | CH$_3$ | CH$_3$ | 6-CH$_3$ | Öl |
| 55 | CH$_3$ | 2-Cl-phenyl | (CH$_3$)$_3$C—C(=O)— | CH$_3$ | CH$_3$ | 6-CH$_3$ | 120 |
| 56 | CH$_3$ | benzyl (—CH$_2$—phenyl) | CH$_3$—C(=O)— | H | Cl | 3-Cl | 124–127 |
| 57 | CH$_3$ | benzyl (—CH$_2$—phenyl) | CH$_3$—C(=O)— | Cl | CF$_3$ | 6-Cl | 105–107 |
| 58 | CH$_3$ | 2-Cl-benzyl | CH$_3$—C(=O)— | H | Cl | 3-Cl | 109–111 |
| 59 | CH$_3$ | 2-Cl-benzyl | CH$_3$—C(=O)— | Cl | CF$_3$ | 6-Cl | 126–129 |
| 60 | CH$_3$ | 2-Cl-benzyl | CH$_3$—C(=O)— | CH$_3$ | CH$_3$ | 6-CH$_3$ | 188 |
| 61 | CH$_3$ | 3-Cl-benzyl | CH$_3$—C(=O)— | H | Cl | 3-Cl | 105–109 |
| 62 | CH$_3$ | 3-Cl-benzyl | CH$_3$—C(=O)— | Cl | CF$_3$ | 6-Cl | 102–104 |

TABLE 2-continued

| Ex. No. | A | B | R | X | Y | Zn | M.p. °C. |
|---|---|---|---|---|---|---|---|
| 63 | CH₃ | 3-Cl-C₆H₄-CH₂- | CH₃-C(=O)- | CH₃ | CH₃ | 6-CH₃ | 125 |
| 64 | CH₃ | 4-Cl-C₆H₄-CH₂- | CH₃-C(=O)- | H | Cl | 3-Cl | 110–115 |
| 65 | CH₃ | 4-Cl-C₆H₄-CH₂- | CH₃-C(=O)- | Cl | CF₃ | 6-Cl | 134–136 |
| 66 | CH₃ | 4-Cl-C₆H₄-CH₂- | CH₃-C(=O)- | CH₃ | CH₃ | 6-CH₃ | 115 |
| 67 | CH₃ | 4-CH₃-C₆H₄-CH₂- | CH₃-C(=O)- | H | Cl | 3-Cl | 90–92 |
| 68 | CH₃ | 4-CH₃-C₆H₄-CH₂- | CH₃-C(=O)- | Cl | CF₃ | 6-Cl | 85 |
| 69 | CH₃ | 3-CF₃-C₆H₄-CH₂- | CH₃-C(=O)- | H | Cl | 3-Cl | 123–125 |
| 70 | CH₃ | 3-CF₃-C₆H₄-CH₂- | CH₃-C(=O)- | Cl | CF₃ | 6-Cl | 120–123 |
| 71 | CH₃ | 3-Cl-C₆H₄-CH₂- | (CH₃)₃C-C(=O)- | CH₃ | CH₃ | 6-CH₃ | 102 |
| 72 | CH₃ | 2-Cl-C₆H₄-CH₂- | (CH₃)₃C-C(=O)- | CH₃ | CH₃ | 6-CH₃ | 79 |
| 73 | CH₃ | C₆H₅-CH₂- | (CH₃)₂CH(CH₂)-C(=O)- | CH₃ | CH₃ | 6-CH₃ | Oil |
| 74 | CH₃ | C₆H₅-CH₂- | (CH₃)₃C-C(=O)- | CH₃ | CH₃ | 6-CH₃ | Oil |

TABLE 2-continued

| Ex. No. | A | B | R | X | Y | Zn | M.p. °C. |
|---|---|---|---|---|---|---|---|
| 75 | CH₃ | (benzyl) -CH₂- | CH₃-C(=O)- | CH₃ | CH₃ | 6-CH₃ | 136 |

PREPARATION OF THE PRECURSORS

Example (II-1)

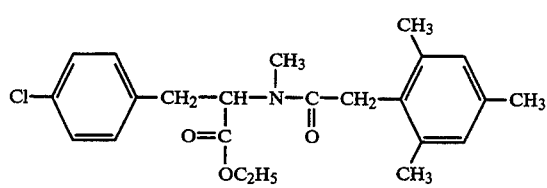

To a solution of 48.3 g (0.20 mol) of 4-chlorophenyl-N-methyl-alanine ethyl ester in 300 ml of absolute tetrahydrofuran and 28 ml of triethylamine there are added dropwise at 0° C. to 10° C. 39.4 g (0.20 mol) of mesityleneacetyl chloride in 40 ml of absolute tetrahydrofuran, and the batch is stirred at room temperature. The end of the reaction is determined by thin-layer chromatography. The batch is then stirred into 1.2 l of ice-water and 200 ml of 1N hydrochloric acid, and the mixture is extracted with dichloromethane. The organic phase is dried and the solvent is distilled off under reduced pressure.

79.91 g (99.4% of Theory) of 2-(4-chlorobenzyl)-N-(2,4,6-trimethylphenylacetyl)-sarcosine ethyl ester are obtained as an oil.

The intermediates of the formula (II)

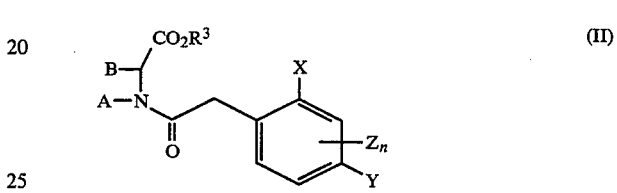

(II)

listed in Table 3 below are obtained analogously to Example (II-1).

TABLE 3

| Ex. No. | A | B | R³ | X | Y | Zn | M.p. °C. |
|---|---|---|---|---|---|---|---|
| II-2 | CH₃ | phenyl | C₂H₅ | CH₃ | CH₃ | 6-CH₃ | |
| II-3 | CH₃ | 2-Cl-phenyl | C₂H₅ | CH₃ | CH₃ | 6-CH₃ | |
| II-4 | CH₃ | 3-Cl-phenyl | C₂H₅ | CH₃ | CH₃ | 6-CH₃ | |
| II-5 | CH₃ | 4-Cl-phenyl | C₂H₅ | CH₃ | CH₃ | 6-CH₃ | |
| II-6 | CH₃ | 4-CH₃-phenyl | C₂H₅ | CH₃ | CH₃ | 6-CH₃ | |
| II-7 | CH₃ | 4-CH₃O-phenyl | C₂H₅ | CH₃ | CH₃ | 6-CH₃ | |
| II-8 | CH₃ | benzyl (-CH₂-phenyl) | C₂H₅ | CH₃ | CH₃ | 6-CH₃ | |

TABLE 3-continued

| Ex. No. | A | B | R³ | X | Y | Zn | M.p. °C. |
|---|---|---|---|---|---|---|---|
| II-9 | CH₃ | 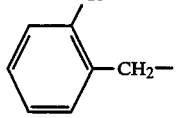 2-Cl-C₆H₄-CH₂- | C₂H₅ | CH₃ | CH₃ | 6-CH₃ | |
| II-10 | CH₃ | 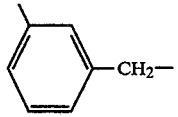 3-Cl-C₆H₄-CH₂- | C₂H₅ | CH₃ | CH₃ | 6-CH₃ | |
| II-11 | CH₃ | 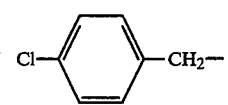 4-Cl-C₆H₄-CH₂- | C₂H₅ | H | Cl | 3-Cl | Oil |
| II-12 | CH₃ | 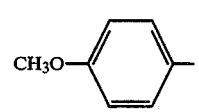 4-CH₃O-C₆H₄- | C₂H₅ | Cl | CF₃ | 6-Cl | 102 |
| II-13 | CH₃ | 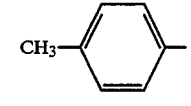 4-CH₃-C₆H₄- | C₂H₅ | Cl | CF₃ | 6-Cl | 146 |
| II-14 | CH₃ | 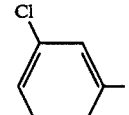 3-Cl-C₆H₄- | C₂H₅ | Cl | CF₃ | 6-Cl | 104 |
| II-15 | CH₃ | 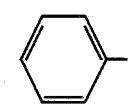 C₆H₅- | C₂H₅ | Cl | CF₃ | 6-Cl | 114 |
| II-16 | CH₃ | 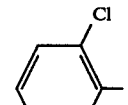 2-Cl-C₆H₄- | C₂H₅ | Cl | CF₃ | 6-Cl | 130 |
| II-17 | CH₃ | 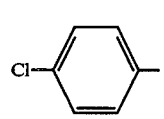 4-Cl-C₆H₄- | C₂H₅ | Cl | CF₃ | 6-Cl | 132 |
| II-18 | CH₃ | 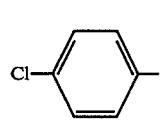 4-Cl-C₆H₄- | C₂H₅ | H | Cl | 3-Cl | 52–54 |
| II-19 | CH₃ | 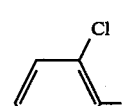 2-Cl-C₆H₄- | C₂H₅ | H | Cl | 3-Cl | 55–57 |
| II-20 | CH₃ | 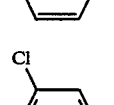 3-Cl-C₆H₄- | C₂H₅ | H | Cl | 3-Cl | 58–60 |

TABLE 3-continued

| Ex. No. | A | B | R³ | X | Y | Zn | M.p. °C. |
|---|---|---|---|---|---|---|---|
| II-21 | CH₃ | 4-CH₃-C₆H₄- | C₂H₅ | H | Cl | 3-Cl | Oil |
| II-22 | CH₃ | 4-CH₃O-C₆H₄- | C₂H₅ | H | Cl | 3-Cl | Oil |
| II-23 | CH₃ | C₆H₅- | C₂H₅ | H | Cl | 3-Cl | Oil |
| II-24 | CH₃ | C₆H₅-CH₂- | C₂H₅ | Cl | CF₃ | 6-Cl | 53–55 |
| II-25 | CH₃ | 2-Cl-C₆H₄-CH₂- | C₂H₅ | Cl | CF₃ | 6-Cl | Oil |
| II-26 | CH₃ | 3-Cl-C₆H₄-CH₂- | C₂H₅ | Cl | CF₃ | 6-Cl | 69–72 |
| II-27 | CH₃ | 3-CF₃-C₆H₄-CH₂- | C₂H₅ | Cl | CF₃ | 6-Cl | 57–61 |
| II-28 | CH₃ | 4-CH₃-C₆H₄-CH₂- | C₂H₅ | Cl | CF₃ | 6-Cl | Oil |
| II-29 | CH₃ | 4-Cl-C₆H₄-CH₂- | C₂H₅ | Cl | CF₃ | 6-Cl | 97–100 |
| II-30 | CH₃ | C₆H₅-CH₂- | C₂H₅ | H | Cl | 3-Cl | Oil |
| II-31 | CH₃ | 2-Cl-C₆H₄-CH₂- | C₂H₅ | H | Cl | 3-Cl | Oil |
| II-32 | CH₃ | 3-Cl-C₆H₄-CH₂- | C₂H₅ | H | Cl | 3-Cl | Oil |

TABLE 3-continued

| Ex. No. | A | B | R³ | X | Y | Zn | M.p. °C. |
|---|---|---|---|---|---|---|---|
| II-33 | CH₃ | CF₃-C₆H₄-CH₂- | C₂H₅ | H | Cl | 3-Cl | Oil |
| II-34 | CH₃ | CH₃-C₆H₄-CH₂- | C₂H₅ | H | Cl | 3-Cl | Oil |

USE EXAMPLES

In the Use Examples which follow, the compound listed below was employed as comparison substance:

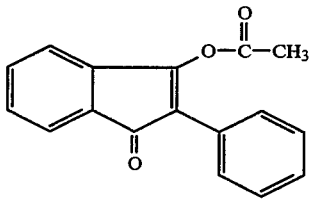

(A)

3-(Acetyloxy)-2-phenyl-1H-inden-1-one (disclosed in U.S. Pat. No. 4,104,043)

EXAMPLE A

Plutella Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, a superior activity compared with the prior art is shown, for example, by the following compounds of the Preparation examples: 1, 5, 8, 17, 23, 32, 35, 44, 52, 53 and 73.

EXAMPLE B

Tetranychus Test (Resistant)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the common spider mite or two-spotted spider mite (*Tetranychus urticae*), are treated by being dipped into the active compound preparation of the desired concentration.

After the specified period of time, the destruction in % is determined. 100% means that all the spider mites have been killed; 0% means that none of the spider mites have been killed.

In this test, a superior activity compared with the prior art is shown, for example, by the following compounds of the Preparation examples: 5, 38, 44, 47, 52, 53, 54 and 73.

EXAMPLE C

Tetranychus Test (OP Resistant)
(OP=Organophosphates)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with a mixed population of the common spider mite or two-spotted spider mite (*Tetranychus urticae*), are treated by being dipped into the active compound preparation of the desired concentration.

After the specified period of time, the mortality in % is determined. 100% means that all the spider mites have been killed; 0% means that none of the spider mites have been killed.

In this test, a superior activity compared with the prior art is shown, for example, by the following compounds of the Preparation examples: 1, 2, 32, 72 and 74.

EXAMPLE D

Erysiphe Test (Barley)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of mildew pustules.

Evaluation is carried out 7 days after the inoculation.

A clearly superior activity compared with the prior art is shown, in this test, for example by the compounds of the following Preparation Examples: 38 and 54.

EXAMPLE E

Antimycotic in-vitro Activity

Experimental set-up

The in-vitro tests were carried out using inocula of $1 \times 10^4$ microorganisms/ml of substrate, on average. The nutrient medium was yeast nitrogen base medium for yeasts and Kimmig medium for moulds and dermatophytes.

The incubation temperature was 37° C. in the case of yeasts and 28° C. in the case of moulds and dermatophytes, and the incubation time was 24 to 96 hours in the case of yeasts and 96 to 120 hours in the case of dermatophytes and moulds.

The fungicides were assessed by plating and reincubation of fully-inhibited batches, fungicidal concentrations containing fewer than 100 colony-forming units per ml.

In this test, the compounds of the formula (I) according to the invention according to the Preparation Examples Nos. 21, 26, 28, 30, 39, 42, 44, 45, 50, 56, 65, 69 show a highly pronounced antimycotic activity.

We claim:

1. Substituted 3-aryl-4-hydroxy-2-ones of the formula (I)

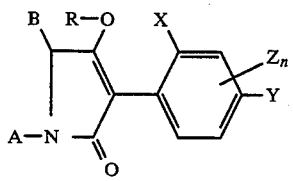

in which

X represents hydrogen, $C_{1-6}$-alkyl, halogen or $C_{1-6}$-alkoxy,

Y represents hydrogen, $C_{1-6}$-alkyl, halogen, $C_{1-6}$-alkoxy or $C_{1-3}$-halogenoalkyl, Z represents $C_{1-6}$-alkyl, halogen or $C_{1-6}$-alkoxy, n represents a number from 0–3, R represents hydrogen (Ia) or the groups of the formula —CO—R$^1$     (Ib)

or

—CO—O—R$^2$     (Ic)

in which

R$^1$ represents optionally halogen-substituted $C_{1-20}$-alkyl, $C_{2-20}$-alkenyl, $C_{1-8}$-alkoxy-$C_{2-8}$-alkyl, $C_{1-8}$-alkylthio-$C_{2-8}$-alkyl, $C_{1-8}$-polyalkoxy-$C_{2-8}$-alkyl or cycloalkyl which has 3–8 ring atoms and which can be interrupted by 1–2 oxygen and/or sulphur atoms, or represents phenyl which is optionally substituted by halogen, nitro, $C_{1-6}$-alkyl, $C_{1-6}$-alkoxy, $C_{1-6}$-halogenoalkyl or $C_{1-6}$-halogenolakoxy, or represents phenyl-$C_{1-6}$-alkyl which is optionally substituted by halogen, $C_{1-6}$-alkyl, $C_{1-6}$-alkoxy, $C_{1-6}$-halogenoalkyl or $C_{1-6}$-halogenoalkoxy, or represents phenoxy-$C_{1-6}$-alkyl which is optionally substituted by halogen or $C_{1-6}$-alkyl, R$^2$ represents optionally halogen-substituted $C_{1-20}$-alkyl, $C_{2-20}$-alkenyl, $C_{1-16}$-alkoxy-$C_{2-6}$-alkyl or $C_{1-8}$-polyalkoxy-$C_{2-8}$-alkyl, or represents phenyl which is optionally substituted by halogen, nitro, $C_{1-6}$-alkyl, $C_{1-6}$-alkoxy or $C_{1-6}$-halogenoalkyl, A represents optionally halogen-substituted straight-chain or branched $C_{1-12}$-alkyl, $C_{3-8}$-alkenyl, $C_{3-8}$-alkinyl, $C_{1-10}$-alkoxy-$C_{2-8}$-alkyl, $C_{1-8}$-polyalkoxy-$C_{2-8}$-alkyl, $C_{1-10}$-alkylthio-$C_{2-8}$-alkyl, cycloalkyl which has 3–8 ring atoms and which can be interrupted by 1–2 oxygen and/or sulphur atoms, or represents aryl-$C_{1-6}$-alkyl which is optionally substituted by halogen, $C_{1-6}$-alkyl, $C_{1-6}$-halogenoalkyl, $C_{1-6}$-alkoxy or nitro, B represents phenyl or benzyl which are optionally monosubstituted or disubstituted by identical or different substituents selected from the group consisting of nitro, halogen, or in each case optionally halogen-substituted $C_{1-4}$-alkyl or $C_{1-4}$-alkoxy, and the pure enantiomeric forms of compounds of the formula (I).

2. Substituted 3-aryl-4-hydroxy-pyrrolidin-2-ones of the formula (I) according to claim 1, in which X represents hydrogen, methyl, ethyl, propyl, i-propyl, fluorine, chlorine, bromine, methoxy and ethoxy, Y represents hydrogen, methyl, ethyl, propyl, i-propyl, butyl, i-butyl, tert.-butyl, fluorine, chlorine, bromine, methoxy, ethoxy and trifluoromethyl, Z represents methyl, ethyl, i-propyl, butyl, i-butyl, tert.-butyl, fluorine, chlorine, bromine, methoxy and ethoxy, n represents a number from 0–3, R represents hydrogen (Ia) or the groups of the formula —CO—R$^1$     (Ib)

or

—CO—O—R$^2$     (Ic)

in which

R$^1$ represents optionally fluorine- or chlorine-substituted $C_1$–$C_{14}$-alkyl, $C_2$–$C_{14}$-alkenyl, $C_1$–$C_4$-alkoxy-$C_2$–$C_6$-alkenyl, $C_1$–$C_4$-alkylthio-$C_2$–$C_6$-alkyl, $C_1$–$C_4$-polyalkoxy-$C_2$–$C_4$-alkyl and cycloalkyl which has 3–6 ring atoms and which can be interrupted by 1–2 oxygen and/or sulphur atoms, or represents phenyl which is optionally substituted bu fluorine, chlorine, bromine, methyl, ethyl, propyl, i-propyl, methoxy, ethoxy, trifluoromethyl, trifluoromethoxy or nitro, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy, or represents phenoxy-$C_1$–$C_4$-alkyl which is optionally substituted by fluorine, chlorine, methyl or ethyl, R$^2$ represents optionally fluorine- or chlorine-substituted $C_1$–$C_{14}$-alkyl, $C_2$–$C_{14}$-alkenyl, $C_1$–$C_4$- alkoxy-$C_2$–$C_6$-alkyl or $C_1$–$C_4$-polyalkoxy-$C_2$–$C_6$-alkyl, or represents phenyl which is optionally substituted by fluorine, chlorine, nitro, methyl, ethyl, propyl, i-propyl, methoxy, ethoxy or trifluoromethyl, A represents optionally halogen-substituted straight-chain or branched $C_1$–$C_8$-alkyl, $C_3$–$C_4$-alkenyl, $C_3$–$C_4$-alkinyl, $C_1$–$C_6$-alkoxy-$C_2$–$C_4$-alkyl, $C_1$–$C_4$-polyalkoxy-$C_2$–$C_4$-alkyl, $C_1$–$C_6$-alkylthio-$C_2$–$C_4$-alkyl or cycloalkyl which has 3–6 ring atoms and which can be interrupted by 1–2 oxygen and/or sulphur atoms, or represents aryl-$C_1$–$C_3$-alkyl which is optionally substituted by fluorine, chlorine, bromine, methyl, ethyl, propyl, iso-propyl, methoxy, ethoxy, trifluoromethyl or nitro, B represents unsubstituted phenyl or benzyl, or represents phenyl or benzyl which are substituted by nitro, fluorine, chlorine or optionally fluorine- or chlorine-substituted $C_1$–$C_2$-alkyl or $C_1$–$C_2$-alkoxy, and the pure enantiomeric forms of compounds of the formula I.

3. Substituted 3-aryl-4-hydroxy-pyrrolidin-2-ones of the formula (I) according to claim 1, in which X represents hydrogen, $C_{1-4}$-alkyl, halogen or $C_{1-6}$-alkoxy, Y represents hydrogen, $C_{1-6}$-alkyl, halogen, $C_{1-4}$-alkoxy or $C_{1-2}$-halogenoalkyl, Z represents $C_{1-4}$-alkyl, halogen or $C_{1-4}$-alkoxy, n represents a number from 0–3, R represents hydrogen (Ia) or the groups of the formula —CO—$R^1$ (Ib)

or

—CO—O—$R^2$ (Ic)

in which $R^1$ represents optionally halogen-substituted $C_{1-16}$-alkyl, $C_{2-16}$-alkenyl, $C_{1-6}$-alkoxy-$C_{2-6}$-alkyl, $C_{1-6}$-alkylthio-$C_{2-6}$-alkyl, $C_{1-6}$-polyalkoxy-$C_{2-6}$-alkyl or cycloalkyl which has 3–7 ring atoms and which can be interrupted by 1–2 oxygen and/or sulphur atoms, or represents phenyl which is optionally substituted by halogen, nitro, $C_{1-4}$-alkyl, $C_{1-4}$-alkoxy, $C_{1-3}$-halogenoalkyl or $C_{1-3}$-halogenolakoxy, or represents phenyl-$C_{1-4}$-alkyl which is optionally substituted by halogen, $C_{1-4}$-alkyl, $C_{1-4}$-alkoxy, $C_{1-3}$-halogenoalkyl or $C_{1-3}$-halogenoalkoxy, or represents phenoxy-$C_{1-5}$-alkyl which is optionally substituted by halogen or $C_{1-4}$-alkyl, $R^2$ represents optionally halogen-substituted $C_{1-16}$-alkyl, $C_{2-16}$-alkenyl, $C_{1-16}$-alkoxy-$C_{2-6}$-alkyl or $C_{1-6}$-polyalkoxy-$C_{2-6}$-alkyl, or represents phenyl which is optionally substituted by halogen, nitro, $C_{1-4}$-alkyl, $C_{1-3}$-alkoxy or $C_{1-3}$-halogenoalkyl, A represents optionally halogen-substituted straight-chain or branched $C_{1-10}$-alkyl, $C_{3-6}$-alkenyl, $C_{3-8}$-alkinyl, $C_{1-8}$-alkoxy-$C_{2-6}$-alkyl, $C_{1-6}$-polyalkoxy-$C_{2-6}$-alkyl, $C_{1-8}$-alkylthio-$C_{2-6}$-alkyl, cycloalkyl which has 3–7 ring atoms and which can be interrupted by 1–2 oxygen and/or sulphur atoms, or represents aryl-$C_{1-4}$-alkyl which is optionally substituted by halogen, $C_{1-4}$-alkyl, $C_{1-4}$-halogenoalkyl, $C_{1-4}$-alkoxy or nitro, B represents phenyl or benzyl which are optionally monosubstituted or disubstituted by identical or different substituents selected from the group consisting of nitro, fluorine, chlorine, bromine, optionally fluorine- or chlorine-substituted $C_{1-4}$-alkyl or $C_{1-4}$-alkoxy, and the pure enantiomeric forms of compounds of the formula (I).

4. A composition for combating insects, acarids, and fungi, said composition comprising an effective amount therefor of a 3-aryl-4-hydroxy-pyrrolidin-2-one in the formula (I) according to claim 1 and a carrier.

5. A method of combating insects, arachnids and fungi, comprising applying an effective amount therefor of a 3-aryl-4-hydroxy-pyrrolidin-2-one of the formula (I) according to claim 1 to said insects, arachnids or fungi or to the habitat of said insects, arachnids of fungi.

6. An antimycotic composition comprising an antimycotically effective amount of a 3-aryl-4-hydroxy-pyrrolidin-2-one of the formula (I) according to claim 1 and a carrier.

* * * * *

UNITED STATES PATENT AND TRADEMARK OFFICE
CERTIFICATE OF CORRECTION

PATENT NO : 5,350,861
DATED : September 27, 1994
INVENTOR(S): Reiner FISCHER, et al.

It is certified that error appears in the above-identified patent and that said Letters Patent is hereby corrected as shown below:

Column 49, line 33,       after "hydroxy" insert --pyrrolidin--

Column 50, line 52,       cancel "alkoxy-$C_2$-$C_6$-alkenyl" and substitute --alkoxy-$C_2$-$C_6$-alkyl--

Column 50, line 57,       cancel "bu" and substitute --by--

Column 51, line 27,       cancel "$C_{1-6}$" and substitute --$C_{1-4}$--

UNITED STATES PATENT AND TRADEMARK OFFICE
CERTIFICATE OF CORRECTION

PATENT NO. : 5,350,861
DATED : September 27, 1994
INVENTOR(S) : Reiner FISCHER, et al.

It is certified that error appears in the above-indentified patent and that said Letters Patent is hereby corrected as shown below:

Column 52, line 36,      cancel "in" and substitute --of--

Column 52, line 5,      cancel "$C_{1-3}$-halogenolakoxy" and substitute --$C_{1-3}$-halogenoalkoxy--

Signed and Sealed this

Sixteenth Day of November, 1999

Attest:

Q. TODD DICKINSON

*Attesting Officer*     *Acting Commissioner of Patents and Trademarks*